United States Patent [19]

Pruckmayr

[11] 4,139,567
[45] Feb. 13, 1979

[54] METHOD FOR PREPARING COPOLYETHER GLYCOLS

[75] Inventor: Gerfried Pruckmayr, Media, Pa.

[73] Assignee: E. I. Du Pont de Nemours and Company, Wilmington, Del.

[21] Appl. No.: 868,112

[22] Filed: Jan. 9, 1978

Related U.S. Application Data

[63] Continuation of Ser. No. 782,737, Mar. 30, 1977, abandoned.

[51] Int. Cl.² ............................................. C07C 41/02
[52] U.S. Cl. .................................. 568/613; 568/622; 568/601
[58] Field of Search ........................................ 260/615 B

[56] References Cited

U.S. PATENT DOCUMENTS

| | | | |
|---|---|---|---|
| 3,254,056 | 5/1966 | Lovell | 260/615 B X |
| 3,282,875 | 11/1966 | Connolly et al. | 260/29.6 |
| 3,359,332 | 12/1967 | Johnston | 260/615 B |
| 3,624,053 | 11/1971 | Gibbs et al. | 260/79.3 |
| 4,038,296 | 7/1977 | Greif et al. | 260/615 B |

FOREIGN PATENT DOCUMENTS

854958 11/1960 United Kingdom ................ 260/615 B

OTHER PUBLICATIONS

USPB 717 Uber die Polymerization destetrahydrofurans, Jan. 11, 1946, 22 pages.

*Primary Examiner*—Howard T. Mars

[57] ABSTRACT

Copolyether glycols are prepared by copolymerizing alkylene oxides or cyclic acetals and tetrahydrofuran, using
(1) a polymeric catalyst which contains sulfonic acid groups; and
(2) a chain terminator which is water or an alkanediol.

7 Claims, No Drawings

METHOD FOR PREPARING COPOLYETHER GLYCOLS

This application is a continuation of copending application Ser. No. 782,737 filed Mar. 30, 1977 now abandoned.

BACKGROUND OF THE INVENTION

Copolyether glycols, i.e., copolymers of alkylene oxides or cyclic acetals with tetrahydrofuran (THF) and end terminated with hydroxyl groups, are well known and useful in the manufacture of polyurethanes. These glycols can be prepared by copolymerizing alkylene oxides or cyclic acetals with THF, using an acid-activated bleaching earth such as montmorillonite clay as a catalyst and water or a polyhydric alcohol as a chain terminator. Such a process is shown in British Pat. No. 854,958.

This method of preparation has not been generally used because the clay particles are quite small and tend to disperse in the reaction medium, and are therefore difficult to separate from the polymer product when the reaction is finished.

It has now been found that copolyether glycols can be prepared by copolymerizing alkylene oxides or cyclic acetals with THF, using (1) a catalyst which, although more complex than that, can for purposes of summary be described as a polymer containing alphafluorosulfonic acid groups; and (2) a chain terminator which is water or an alkanediol of 2 to 10 carbon atoms.

The physical nature of the catalyst and its low solubility in the reaction mass makes it easy to separate from the product at the end of the polymerization reaction and therefore makes the process especially suited for being run in a continuous fashion. The catalyst's low solubility also minimizes catalyst loss as the reaction proceeds.

SUMMARY OF THE INVENTION

The process of the invention comprises simply bringing the alkylene oxides, the THF and the catalyst together under conditions suitable for copolymerization, and then, when the proper molecular weight has been attained, terminating the polymerization.

The reaction involved is shown in the following illustrative equations:

In these equations

P represents the polymer segment of the catalyst;

R is an hydroxyalkyl group of 2 to 10 carbon atoms; and

~~~represents the copolyether chain.

When the reactions are complete, the catalyst can be separated from the reaction mass and reused.

DETAILED DESCRIPTION OF THE INVENTION

The alkylene oxides used are those of 2 to 10 carbon atoms. Illustrative of these are ethylene oxides, propylene oxide, 1,2-butylene oxide and 1,3-butylene oxide. Ethylene oxide and propylene oxide are preferred for their availability. The cyclic acetals used are those represented by the structure where n is 1 to 4 and X is hydrogen or an alkyl radical of 1 to 4 carbon atoms.

Mixtures of oxides and mixtures of oxides and acetals can also be used. The oxides and acetals can be any of those commercially available and need be of no special type or purity.

The THF used can likewise be any of those commercially available, but preferably is dry, i.e., has a water content of less than about 0.001%, by weight, a peroxide content of less than 0.002%, by weight, and contains an oxidation inhibitor such as butylated hydroxytoluene to prevent formation of undesirable byproducts and color.

If desired, 0.1 to 50% by weight of the THF of an alkyl tetrahydrofuran, copolymerizable with THF, can be used as a coreactant. Such an alkyl THF can be represented by the structure where any one of $R_1$, $R_2$, $R_3$ or $R_4$ is an alkyl radical of 1 to 4 carbon atoms, the remaining R's being hydrogen.

Illustrative of such alkyl tetrahydrofurans are 2-methyl tetrahydrofuran and 3-methyl tetrahydrofuran.

The catalysts used in the process of the invention are polymers of ethylenically unsaturated monomers containing groups of the formula

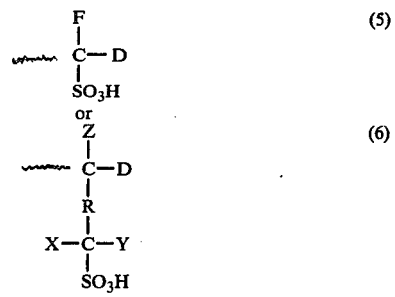

where

~~~ represents the polymer chain or a segment thereof;

D is hydrogen, an aliphatic or aromatic hydrocarbon radical of 1 to 10 carbon atoms, a halogen atom or a segment of the polymer chain;

X and Y are hydrogen, an aliphatic or aromatic hydrocarbon radical of 1 to 10 carbon atoms or fluorine, but at least one must be fluorine;

R is a linear or branched linking group having up to 40 carbon atoms in the principal chain, and Z is hydrogen, an aliphatic or aromatic hydrocarbon radical of 1 to 10 carbon atoms or halogen.

The linking group defined by R in formula (6) can be a homogeneous one such as an alkylene radical, or it can be a heterogeneous one such as an alkylene ether radical. In the preferred catalysts, this linking radical contains 1 to 20 carbon atoms in the principal chain. In the especially preferred catalyst, R is a radical of the structure

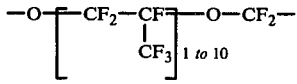

The catalysts of formulas (5) and (6) have equivalent weights of 950 to 1,500, preferably 1,100 to 1,300. Equivalent weight of a catalyst is that weight in grams which contains one gram equivalent weight of sulfonic acid groups, and can be determined by titration.

Illustrative of the ethylenically unsaturated monomers which can be used to prepare these polymer chains are ethylene, styrene, vinyl chloride, vinyl fluoride, vinylidene fluoride, chlorotrifluoroethylene (CTFE), bromotrifluoroethylene, vinyl ethers, perfluoroalkyl vinyl ethers, tetrafluoroethylene, hexafluoropropylene, and combinations of these.

The —SO₃H groups are introduced into the catalyst polymer chain by copolymerizing these ethylenically unsaturated monomers with such ethylenically unsaturated monomers as trifluorovinyl sulfonic acid, linear or branched chain vinyl monomers containing sulfonic acid group precursors or perfluoroalkylvinyl ethers containing sulfonic acid group precursors. This can be done according to the procedures described in U.S. Pat. No. 3,784,399 to Grot, and the patents cited therein. Monomer ratios are selected to give the resulting polymer the proper equivalent weight.

The catalyst preferably has a solubility such that no more than about 5%, by weight, dissolves in the reaction mass at the reaction temperature. This solubility is determined gravimetrically.

It is desirable that the solubility of the catalyst be as low as possible because this minimizes catalyst loss and permits the process to be run for longer periods without catalyst replenishment. Preferably, the solubility is no more than about 1%, by weight, and even more preferably is below the threshold of detection with present analytical techniques.

The catalyst should be effectively free of functional groups, other than -SO₃H groups, which might interfere with the polymerization reaction. "Effectively free" means the catalyst may contain a small number of such groups, but not so many that the reaction is affected adversely or the product contaminated. Illustrative of such groups are carboxyl groups, hydroxyl groups and amino groups.

Catalysts whose polymer chains are of fluorocarbon monomers are preferred for use in the process of the invention. Illustrative of such monomers are tetrafluoroethylene (TFE), hexafluoropropylene, CTFE, bromotrifluoroethylene and perfluoroalkyl vinyl ethers. Mixtures of monomers can also be used.

Even more preferred as catalysts are copolymers of TFE or CTFE and a perfluoroalkyl vinyl ether containing sulfonic acid group precursors. Most preferred in this class are copolymers of TFE or CTFE and a monomer represented by the structure

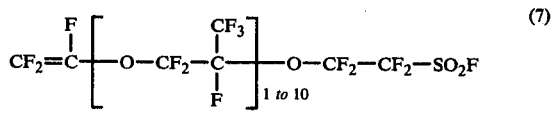

These polymers are prepared in the sulfonyl fluoride form and are then hydrolyzed to the acid form, as described in U.S. Pat. No. 3,692,569.

Most preferred as catalysts are copolymers of TFE and monomers of formula (7) in which the respective monomer weight ratios are 50-75/25-50. Such copolymers, having equivalent weights of 1100, 1150 and 1500, are sold by E. I. duPont de Nemours and Company as Nafion ® perfluorosulfonic acid resins.

The chain terminator used in the process of the invention can be water or an alkanediol of 2 to 10 carbon atoms. Water and 1,4-butanediol are preferred for their availability and low cost.

The copolymerization reaction is carried out by first charging a reactor with THF, an alkylene oxide or cyclic acetal and catalyst.

The amounts of alkylene oxide and THF in the reaction mass can be varied to provide copolymers having alkylene oxide or cyclic acetal/THF weight ratios of 1-90/10-99, as is well known in the art. The ratio for any given copolymer is, of course, dictated by its use.

The catalyst concentration in the reaction mass can range from about 0.1% to about 10%, by total weight of the monomers present, preferably 5 to 10%. It has been found that use of a dry catalyst significantly increases reaction speed. It is best that the catalyst be as dry as possible, but removing all the water is difficult, so in the usual case the catalyst is first dried by holdng it at about 110° C. and a pressure of about 0.1 mm of mercury until it reaches constant weight, or by azeotropically distilling it with a liquid hydrocarbon.

The reaction mass is then held, with stirring or agitation, at a temperature ranging from ambient temperature to the boiling point of THF, preferably 20° to 60° C. If higher reaction temperatures are desired, the reaction can be run at pressures of up to about 5,000 atmospheres. The reaction is preferably run in an inert atmosphere, such as nitrogen.

Polymerization is allowed to continue until a copolymer with the desired molecular weight has been obtained, as found by periodic sampling and analysis by end group determination. This point is ordinarily reached in 2 to 48 hours, the time depending, of course, on the reaction temperature and the catalyst concentration.

The polymerization reaction is then stopped by adding to the reaction mass a stoichiometric excess of the chain terminator. The catalyst can then be easily separated from the reaction mass by filtration, centrifugation or decantation, dried and reused.

The process of the invention can be run batchwise or continuously. When run continuously, the THF, alkylene oxide or cyclic acetal, chain terminator and optionally, catalyst, are continuously fed into a reactor at rates which provide the requisite concentrations and which provide a suitable residence time, and copolymer product and excess reactants are continuously removed. Preferably, the catalyst is charged initially and is held in the reaction zone by suitable screens or filters, and can remain in continuous use.

After the reaction mass is withdrawn from the reactor, whether it be a batch reactor or a continuous reactor, it is separated from unreacted THF, unreacted alkylene oxide or cyclic acetal and unreacted chain terminator by conventional techniques, to give the copolyether product.

EXAMPLES

EXAMPLE 1

Nafion ® resin, equivalent weight 950, was dried to constant weight at 110° C. under a vacuum of 0.1 mm of mercury, and 2.6 g of this catalyst were then mixed with 100 g of THF that had been dried over sodium. This mixture was held, with stirring, at 25° C., in a nitrogen atmosphere, in a polymerization kettle equipped with drying tubes to exclude moisture, while gaseous ethylene oxide was slowly bubbled in over a two-hour period. This reaction mixture was held at 25° C., with stirring, for 15 hours, at which point 100 ml of a 9:1 (by volume) mixture of THF and water were added.

The catalyst was removed from the mixture by filtration, and unreacted THF was removed from the filtrate by distillation under reduced pressure. The filtrate was then added to toluene, and residual water was removed by azeotropic distillation at atmospheric pressure. Toluene was driven from the residue by holding it at 80° C. under a pressure of 0.1 mm of mercury, to give 26 g of copolyether glycol product containing 18 mol percent of ethylene oxide units, as determined by nuclear magnetic resonance spectroscopy.

EXAMPLE 2

Ten grams of Nafion ® resin, equivalent weight 1100, was dried by mixing the resin with THF and then azeotropically distilling off the water. When the boiling point of the distillate reached 64° C., distillation was discontinued and the THF/Nafion ® weight ratio was adjusted to 10/1.

The mixture was held, with stirring, at 25° C., in a nitrogen atmosphere, in a polymerization kettle equipped with drying tubes to exclude moisture, while 10 g of propylene oxide were slowly added, dropwise. The mixture was then stirred at 25° C. for 15 hours, at which point about 100 ml of a THF/water 2:1 (volume) mixture were added.

The catalyst was removed from the mixture by filtration, and unreacted THF was removed from the filtrate by distillation under reduced pressure. The filtrate was then added to toluene, and residual water was removed by azeotropic distillation at atmospheric pressure. Toluene was driven from the residue by holding it at 80° C. under a pressure of 0.1 mm of mercury, to give 20 g of copolyether glycol product containing 21 mol percent of propylene oxide units, as determined by nuclear magnetic resonance spectroscopy.

I claim:

1. In a process for preparing a copolyether glycol by copolymerizing an alkylene oxide or a cyclic acetal and tetrahydrofuran using water or an alkanediol as a chain terminator, the improvement comprising using as a catalyst a polymer of monoethylenically unsaturated monomers, the polymer containing groups of the formula

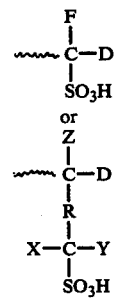

where
~ represents the polymer chain or a segment thereof;
D is hydrogen, an aliphatic or aromatic hydrocarbon radical of 1 to 10 carbon atoms, a halogen or a segment of the polymer chain;
X and Y are hydrogen, an aliphatic or aromatic hydrocarbon radical of 1 to 10 carbon atoms, or fluorine, but at least one of X and Y must be fluorine;
R is a linear or branched linking group having up to 40 carbon atoms in the principal chain; and
Z is hydrogen, an aliphatic or aromatic hydrocarbon radical of 1 to 10 carbon atoms, or halogen;
the polymer being effectively free of functional groups which interfere with the reaction.

2. The process of claim 1 wherein the catalyst is a polymer of fluorocarbon monomers.

3. The process of claim 2 wherein the catalyst is a copolymer of tetrafluoroethylene or chloritrifluoroethylene and R is

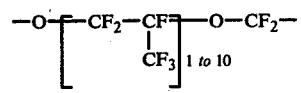

4. The process of claim 3 wherein the catalyst is a hydrolyzed copolymer of tetrafluoroethylene or chlorotrifluoroethylene and a monomer represented by the structure

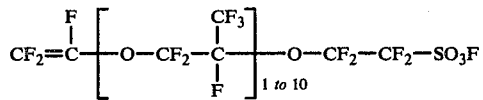
the tetrafluoroethylene or chlorotrifluoroethylene and monomer units being present in weight ratios of 50–75/25–50, respectively.
5. The process of claim 1 wherein the alkylene oxide is ethylene oxide.
6. The process of claim 1 wherein the alkylene oxide is propylene oxide.
7. The process of claim 1 wherein the chain terminator is water.